United States Patent [19]

Gammill

[11] Patent Number: 4,532,340
[45] Date of Patent: Jul. 30, 1985

[54] FUROCHROMONE INTERMEDIATES

[75] Inventor: Ronald B. Gammill, Portage, Mich.

[73] Assignee: The Upjohn Company, Kalamazoo, Mich.

[21] Appl. No.: 545,988

[22] Filed: Oct. 27, 1983

Related U.S. Application Data

[62] Division of Ser. No. 378,687, May 17, 1982, Pat. No. 4,434,296.

[51] Int. Cl.$^3$ .................. C07D 307/86; C07D 307/54
[52] U.S. Cl. ...................................... 549/471; 549/486
[58] Field of Search ................................ 549/471, 486

[56] References Cited

U.S. PATENT DOCUMENTS

| | | | |
|---|---|---|---|
| 2,680,119 | 6/1954 | Robertson et al. | 260/345.2 |
| 4,284,569 | 8/1981 | Gammill | 260/345.2 |

OTHER PUBLICATIONS

R. Aneja, et al., A New Synthesis of Khellin, J. Sci. Industr. Res., 17B:382–383 (1958).
R. Aneja, et al., Neue Synthesen vol Khellin, Chem. Ber., 93:297–303 (1960).
R. A. Baxter, et al., Furochromones, Part I, The Synthesis of Khellin, J. Chem. Soc., pp. S30–S33 (1949).
J. R. Clarke, et al., Furano–Compounds, Part Ix, The Synthesis of Khellin and Related Compounds, J. Chem. Soc., pp. 302–307 (1949).
O. Dann, et al., Eine Neue Synthese von Khellin and Anderen Furo-2-Methyl-Chromonen, Ann. Chem. 605:146–157 (1957).
O. Dann, et al., Synthese von 2-Methyl-5,8-Dihydroxy-Furano-[3'.2':6.7]-Chromon und von Khellin, Chem. Berg., 93:2829–2833, (1960).
T. S. Gardner, et al., The Synthesis of Khellin Derivatives, J. Org. Chem., 15:841–849 (1950).
T. A. Geissman, et al., Chromones, III, A Total Synthesis of Khellin, J. Amer. Chem. Soc., 73:1280–1284 (1951).
V. V. S. Murti, et al., A Synthesis of Kellin, J. Sci. Ind. Res. (India) 8B:112–113, (1949).
V. V. S. Murti, et al., Nuclear Oxidation of Flavones and Related Compounds Part XXIII, Proc. of the Indian Acad. of Sci., 30A:107–113, (1949).
C. Musante, Prodotti di Scissione Alcalina della Khellina e Loro Derivati e transsformazione del Sistema del Furo–Cromone in quello del Furo–benzoisossazolo, Gazz. Chim. Ital., 88:910–929, (1958).
A. Mustafa, Furopyrans and Furopyrones, Chapter III, Furochromones, John Wiley and Sons, Inc., New York, pp. 102–159 (1967).
A. Mustafa, Benzofurans, John Wiley and Sons, 1974.
L. R. Row et al., Furanobenzopyrones: Part VII, Indian J. Chem., 5:105–106 (1967).
A. Schonberg, et al., Khellin from Visnagin, J. Amer. Chem. Soc., 73:2960–2961 (1951).
E. Spath, et al., Die Konstitution des Kellins, Chem. Ber., 71:106–113 (1938).

Primary Examiner—Henry R. Jiles
Assistant Examiner—Bernard I. Dentz
Attorney, Agent, or Firm—Lawrence T. Welch; Martha A. Cox

[57] ABSTRACT

The present invention provides novel intermediates used for preparation of anti-atherosclerotic furochromones.

8 Claims, No Drawings

FUROCHROMONE INTERMEDIATES

CROSS REFERENCE TO RELATED APPLICATIONS

The present application is a division of co-pending application Ser. No. 378,687, filed May 17, 1982, now U.S. Pat. No. 4,434,296.

BACKGROUND OF THE INVENTION

The present invention relates to novel compounds which are intermediates used for the preparation of furochromones which are useful as anti-atherosclerotic agents. The preparation and use of these compounds is described in U.S. Pat. No. 4,434,296, which is expressly incorporated by reference herein.

PRIOR ART

Methods for the total synthesis of khellin are known, as are described in U.S. Pat. No. 4,434,296.

Most typically, however, the total synthesis of furochromones from benzofurans has been accomplished by utilizing a substituted benzene ring from which to synthesize the fused benzopyran ring system. See. Mustafa, "Benzofurans," John Wiley and Sons, 1974, and Mustafa, "Furopyrans and Furopyrones, Chapter 3: Furochromones," John Wiley and Sons, N.Y., N.Y. (1967).

U.S. Pat. No. 4,284,569 provides a variety of novel antiatherosclerotic furochromones.

SUMMARY OF THE INVENTION

The present invention provides:
(a) a furochromone intermediate of formula I or II wherein $R_{11}$ is $(C_1-C_4)$alkyl;
  wherein $R_2$ is hydrogen or $C_1-C_4$ alkyl; and
  wherein W is $\alpha$-H:$\beta$-H or =CH—NR$_3$R$_4$;
  wherein $R_3$ and $R_4$, being the same or different, are $C_1-C_4$ alkyl;
(b) a furochromone intermediate of formula III;
(c) a furochromone intermediate of formula IV;
  wherein $R_{11}$ is $C_1-C_4$ alkyl;
(d) a furochromone intermediate of formula V;
  wherein $R_{11}$ is $C_1-C_4$ alkyl and
  wherein $R_3$ and $R_4$, being the same or different, are $C_1-C_4$ alkyl;
(e) a furochromone intermediate of formula VI:
  wherein $R_{11}$ is $C_1-C_4$ alkyl; and
(f) a furochromone intermediate of formula VII:
  wherein $R_1$ and $R_{11}$ are $C_1-C_4$ alkyl.

DESCRIPTION OF THE PREFERRED EMBODIMENTS

The present invention particularly provides:
3-carboxy-$\gamma$-oxo-2-furanbutanoic acid;
3-carboxy-$\gamma$-oxo-2-furanbutanoic acid bis (methyl ester);
$\beta$-[(dimethylamino)methylene]-3-(methoxycarbonyl)-$\gamma$-oxo-2-furobutanoic acid bis (methyl ester);
6-formyl-4,7-dihydroxy-5-benzofurancarboxylic acid, methyl ester;
6-formyl-4,7-dimethoxy-5-benzofurancarboxylic acid, methyl ester;
6-hydroxy-4,7-dimethoxy-5-benzofurancarboxylic acid, methyl ester; and
1-(6-hydroxy-4,7-dimethoxy-5-benzofuranyl)-ethanone.

I claim:

1. A furochromone intermediate of formula I or II:

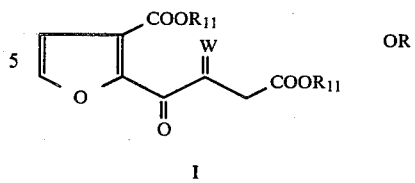

I

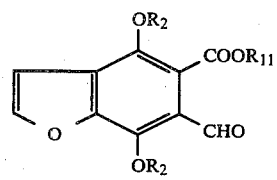

II wherein $R_{11}$ is $(C_1-C_4)$alkyl;
wherein $R_2$ is hydrogen or $C_1-C_4$ alkyl; and
wherein W is $\alpha$-H:$\beta$-H or =CH—NR$_3$R$_4$;
wherein $R_3$ and $R_4$, being the same or different, are $C_1-C_4$ alkyl.

2. A furochromone intermediate of formula III:

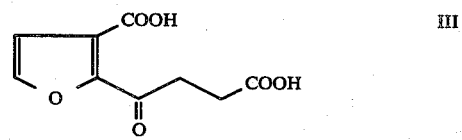

III

3. A furochromone intermediate according to claim 1 of formula IV:

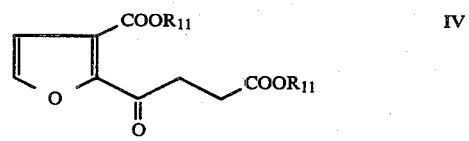

IV wherein $R_{11}$ is $C_1-C_4$ alkyl.

4. A furochromone intermediate according to claim 1 of formula V:

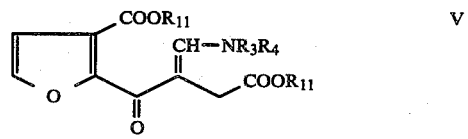

V wherein $R_{11}$ is $C_1-C_4$ alkyl and
wherein $R_3$ and $R_4$, being the same or different, are $C_1-C_4$ alkyl.

5. A furochromone intermediate according to claim 1 of formula VI:

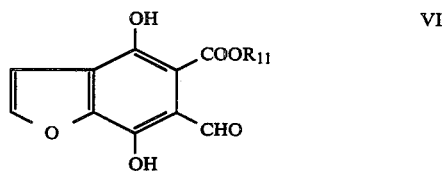

VI wherein $R_{11}$ is $C_1-C_4$ alkyl.

6. A furochromone intermediate according to claim 1 of formula VII:

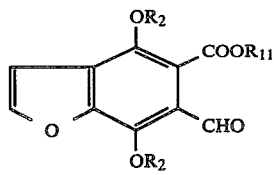

wherein $R_2$ and $R_{11}$ are $C_1$–$C_4$ alkyl.

7. A furochromone intermediate according to claim 1 wherein $R_2$ and $R_{11}$ are methyl.

8. A compound of claim 1 selected from the group consisting of
3-carboxy-γ-oxo-2-furanbutanoic acid bis (methyl ester);
β-[(dimethylamino)methylene]-3-(methoxycarbonyl)-γ-oxo-2-furanbutanoic acid (methyl ester);
6-formyl-4,7-dihydroxy-5-benzofurancarboxylic acid, methyl ester; and
6-formyl-4,7-dimethoxy-5-benzofurancarboxylic acid, methyl ester.

* * * * *